United States Patent
Williams et al.

(10) Patent No.: US 10,595,870 B2
(45) Date of Patent: Mar. 24, 2020

(54) ANVIL ASSEMBLY WITH FRANGIBLE RETAINING MEMBER

(71) Applicant: Covidien LP, Mansfield, MA (US)

(72) Inventors: Justin Williams, Southbury, CT (US); Patrick D. Mozdzierz, Glastonbury, CT (US); Steven Joyce, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 462 days.

(21) Appl. No.: 15/387,794

(22) Filed: Dec. 22, 2016

(65) Prior Publication Data
US 2017/0100124 A1    Apr. 13, 2017

Related U.S. Application Data

(63) Continuation of application No. 14/078,766, filed on Nov. 13, 2013, now Pat. No. 9,554,802.

(51) Int. Cl.
*A61B 17/115* (2006.01)
*A61B 90/00* (2016.01)

(52) U.S. Cl.
CPC ..... *A61B 17/1155* (2013.01); *A61B 2090/037* (2016.02)

(58) Field of Classification Search
CPC ............. A61B 17/1155; A61B 2090/037
USPC ..... 227/19, 175.1–182.1; 606/139, 219, 153, 606/75, 220
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| | | |
|---|---|---|
| CA | 908529 A | 8/1972 |
| DE | 1057729 B | 5/1959 |

(Continued)

OTHER PUBLICATIONS

Chinese Office Action dated Feb. 2, 2018, issued in CN Appln. No. 201410641539.

(Continued)

*Primary Examiner* — Gloria R Weeks
*Assistant Examiner* — Dariush Seif
(74) *Attorney, Agent, or Firm* — Carter, DeLuca & Farrell LLP

(57) ABSTRACT

An anvil assembly includes a retaining member having a body portion and a frangible portion connected to the body portion, where the frangible portion is positioned to engage a backup member and separates from the body portion during movement of the backup member from a first, proximal position to a second, distal position. The retaining member keeps the backup plate in the proximal position prior to firing of the stapling assembly, and upon separation of the frangible portion allows the backup plate to move to the distal position during firing of the stapling assembly. Proximal force on the backup plate after firing of the stapling assembly is avoided, thereby helping to ensure titling of the anvil assembly.

20 Claims, 7 Drawing Sheets

(56) References Cited

U.S. PATENT DOCUMENTS

| | | | |
|---|---|---|---|
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A * | 3/1985 | Utyamyshev | A61B 17/115 227/155 |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,929,240 A * | 5/1990 | Kirsch | A61B 17/083 606/142 |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A * | 6/1993 | Brinkerhoff | A61B 17/11 227/179.1 |
| 5,250,058 A * | 10/1993 | Miller | A61B 17/11 24/615 |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A * | 5/1994 | Welch | A61B 17/0218 128/898 |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A * | 11/1997 | Seeber | A61B 17/115 227/175.1 |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,131,789 A * | 10/2000 | Schulze | A61B 17/07207 227/175.2 |
| 6,142,933 A | 11/2000 | Longo et al. | |
| 6,149,667 A | 11/2000 | Hovland et al. | |
| 6,176,413 B1 | 1/2001 | Heck | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |

(56) References Cited

U.S. PATENT DOCUMENTS

| | | |
|---|---|---|
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 * | 4/2008 | Milliman ............ A61B 17/068 227/175.1 |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |

(56) References Cited

U.S. PATENT DOCUMENTS

| | | |
|---|---|---|
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,272,552 B2 | 9/2012 | Holsten et al. |
| 8,317,073 B2 | 11/2012 | Milliman et al. |
| 8,328,063 B2 | 12/2012 | Milliman et al. |
| 8,343,185 B2 | 1/2013 | Milliman et al. |
| 8,360,295 B2 | 1/2013 | Milliman et al. |
| 8,403,942 B2 | 3/2013 | Milliman et al. |
| 8,418,905 B2 | 4/2013 | Milliman |
| 8,424,535 B2 | 4/2013 | Hessler et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,590,763 B2 | 11/2013 | Milliman |
| 8,608,047 B2 | 12/2013 | Holsten et al. |
| 8,616,428 B2 | 12/2013 | Milliman et al. |
| 8,616,429 B2 | 12/2013 | Viola |
| 8,631,993 B2 | 1/2014 | Kostrzewski |
| 9,554,802 B2 | 1/2017 | Williams et al. |
| 2003/0111507 A1 | 6/2003 | Nunez |
| 2003/0178463 A1* | 9/2003 | Jablonski ............... B25C 1/005 227/120 |
| 2005/0051597 A1 | 3/2005 | Toledano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2005/0149075 A1* | 7/2005 | Borghi ................... A61B 17/11 606/153 |
| 2005/0149076 A1* | 7/2005 | Borghi ................... A61B 17/11 606/153 |
| 2005/0187576 A1 | 8/2005 | Whitman et al. |
| 2005/0205639 A1* | 9/2005 | Milliman ............. A61B 17/115 227/175.1 |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0230581 A1* | 9/2008 | Marczyk ............. A61B 17/115 227/176.1 |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1* | 1/2011 | Kostrzewski ........ A61B 17/115 227/176.1 |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2012/0080498 A1* | 4/2012 | Shelton, IV ...... A61B 17/00491 227/178.1 |
| 2012/0104073 A1 | 5/2012 | Milliman et al. |
| 2012/0125972 A1 | 5/2012 | Holsten et al. |
| 2012/0145766 A1 | 6/2012 | Milliman et al. |
| 2012/0153005 A1 | 6/2012 | Milliman |
| 2012/0168487 A1 | 7/2012 | Holsten et al. |
| 2012/0193395 A1 | 8/2012 | Pastorelli et al. |
| 2012/0193398 A1 | 8/2012 | Williams et al. |
| 2012/0228356 A1 | 9/2012 | Milliman et al. |
| 2012/0228357 A1 | 9/2012 | Milliman |
| 2012/0232339 A1 | 9/2012 | Csiky |

(56) References Cited

U.S. PATENT DOCUMENTS

| | | |
|---|---|---|
| 2012/0248173 A1 | 10/2012 | Milliman et al. |
| 2012/0273548 A1 | 11/2012 | Ma et al. |
| 2012/0280018 A1 | 11/2012 | Hessler et al. |
| 2012/0292368 A1 | 11/2012 | Nalagatla et al. |
| 2012/0298721 A1 | 11/2012 | Bettuchi et al. |
| 2012/0305625 A1 | 12/2012 | Milliman et al. |
| 2012/0305629 A1 | 12/2012 | Orban, III et al. |
| 2012/0325888 A1 | 12/2012 | Qiao et al. |
| 2012/0325892 A1 | 12/2012 | Kostrzewski |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0037599 A1 | 2/2013 | Rebuffat et al. |
| 2013/0048308 A1* | 2/2013 | Lehr .................... E21B 43/103 166/378 |
| 2013/0056516 A1 | 3/2013 | Viola |
| 2013/0056517 A1 | 3/2013 | Patel et al. |
| 2013/0060258 A1 | 3/2013 | Giacomantonio |
| 2013/0068817 A1 | 3/2013 | Milliman et al. |
| 2013/0068819 A1 | 3/2013 | Viola |
| 2013/0105544 A1* | 5/2013 | Mozdzierz ......... A61B 17/1155 227/175.1 |
| 2013/0105546 A1 | 5/2013 | Milliman et al. |
| 2013/0105549 A1 | 5/2013 | Holsten et al. |
| 2013/0105551 A1 | 5/2013 | Zingman |
| 2013/0126580 A1 | 5/2013 | Smith et al. |
| 2013/0126587 A1 | 5/2013 | Bettuchi et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181029 A1 | 7/2013 | Milliman |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1* | 8/2013 | Carter ............... A61B 17/07292 227/179.1 |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367444 A1* | 12/2014 | Williams ............ A61B 17/1155 227/175.1 |
| 2014/0367450 A1* | 12/2014 | Williams ............. A61B 17/115 227/181.1 |
| 2015/0083772 A1* | 3/2015 | Miller ................. A61B 17/1155 227/175.1 |
| 2015/0129635 A1* | 5/2015 | Williams ............ A61B 17/1155 227/177.1 |
| 2016/0106430 A1* | 4/2016 | Carter ................. A61B 17/072 227/176.1 |
| 2016/0157855 A1* | 6/2016 | Williams ............ A61B 17/1155 227/180.1 |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2524656 A2 | 11/2012 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |

OTHER PUBLICATIONS

Australian Office Action dated Jun. 21, 2018 in AU Appln. No. 2014227481.

European Search Report EP14192780 dated Feb. 24, 2015.

* cited by examiner

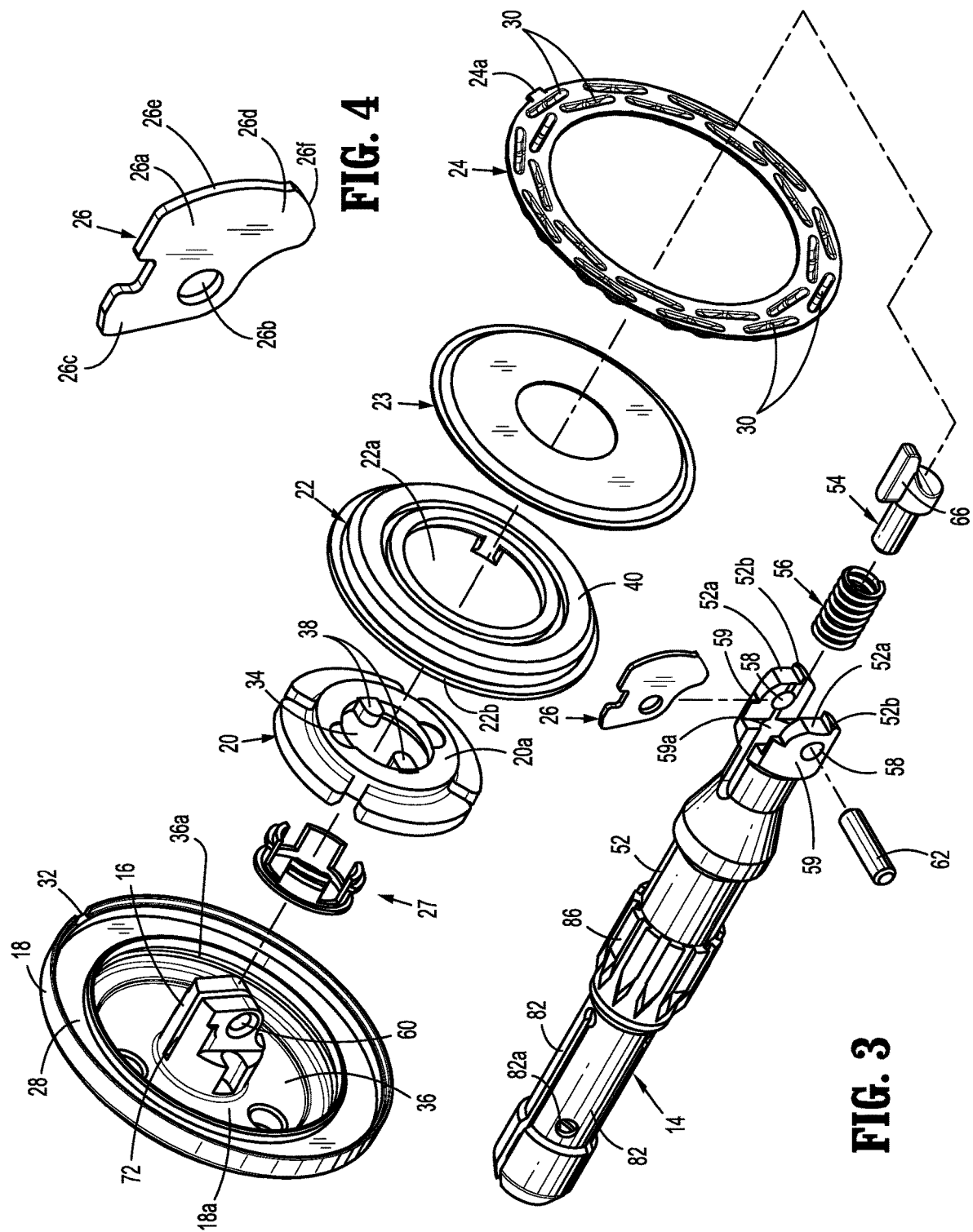

ANVIL ASSEMBLY WITH FRANGIBLE RETAINING MEMBER

CROSS-REFERENCE TO RELATED APPLICATIONS

This is a continuation application and claims the benefit of and priority to U.S. patent application Ser. No. 14/078,766 filed Nov. 13, 2013, the entire disclosure of which is incorporated by reference herein.

BACKGROUND

Technical Field

The present disclosure relates generally to an anvil assembly having a tiltable head which is suitable for use with a circular anastomosis stapler. More specifically, the present disclosure relates a tiltable anvil assembly having a frangible retaining member.

Background of Related Art

Circular anastomosis staplers which include an anvil assembly having a tiltable anvil head are known in the art. An example of such circular anastomosis stapler and tiltable anvil assembly are disclosed in commonly owned U.S. Pat. No. 7,364,060 ("the '060 patent"). A further example of a tiltable anvil assembly is disclosed in commonly owned U.S. Patent Application Publication No. 2008/0230581 ("the '581 publication"). The content of each of the '060 patent and the '581 publication are hereby incorporated herein by reference in their entirety. The anvil assembly described in the '581 publication includes a backup plate located within the anvil assembly positioned to prevent tilting of the anvil head of the anvil assembly prior to firing of the stapler. Upon firing of the stapler, a knife blade of the stapler engages and moves the backup plate to a position which allows the anvil head to tilt upon retraction of the knife blade. If the backup plate sticks to the knife blade upon retraction of the knife blade, the backup plate may return to its position preventing tilting of the anvil head. When this occurs, the anvil head will not tilt.

In order to maintain the backup plate in a proximal position where it prevents tilting of the anvil head prior to firing, the anvil assembly described in the '581 publication includes a retainer member positioned distal of the backup plate. The retainer member includes a plurality of deformable tabs which prevent distal movement of the backup plate until a predetermined force sufficient to deform the tabs is applied to the backup plate, i.e., through engagement with the knife blade during staple formation. A residual proximal force is produced during deformation of the deformable tabs. This force acts on the backup plate which may cause the backup plate to move proximally towards its original position. As described in the '581 publication, the tilting operation of the anvil assembly relies on the distal positioning of the backup plate following the firing of the stapler. Any proximal force that acts on the backup plate may cause the backup plate to return to the original proximal position, thereby preventing tilting of the anvil assembly.

Therefore, it would be beneficial to provide an anvil assembly with a means of retaining the backup plate in the proximal position prior to firing of the stapling assembly, that allows the backup plate to move to the distal position during firing of the stapling assembly, and that does not produce a proximal force which acts on the backup plate after firing of the stapling assembly that may prevent the anvil assembly from tilting.

SUMMARY

Accordingly, an anvil assembly is provided. The anvil assembly includes a center rod assembly and a head assembly. The head assembly includes a housing, a backup member, and a retaining member. The head assembly is pivotally supported on the center rod assembly between a non-tilted position and a tilted position. The backup member is movable from a first position in which a portion of the backup member is positioned to prevent pivotal movement of the head assembly from the non-tilted position to the tilted position, to a second position in which the backup member is positioned to permit pivotal movement of the head assembly in relation to the center rod assembly from the non-tilted position to the tilted position. The retaining member includes a body portion and a frangible portion connected to the body portion. The frangible portion is positioned to engage the backup member and is configured to separate from the body portion during movement of the backup member from the first position to the second position.

In one embodiment, the retainer member is positioned in the head assembly to prevent movement of the backup member from the first position to the second position until a predetermined force has been applied to the backup member. The retainer member may be positioned in the head assembly between the housing and the backup member, the retainer member including a retaining portion and a body portion extending from the retaining portion, the frangible portion being supported on the body portion spaced from the retaining portion. The retaining portion of the retainer member may be positioned adjacent an inside wall of the housing. The head assembly may further include a post, the housing and the post defining an annular recess and the retainer member being positioned in the annular recess. The retainer member may include a retaining portion formed on a first end of the body portion and the frangible portion is supported on the body portion at a location spaced from the retaining portion. The body portion of the retainer member may define a plurality of cutouts configured to accommodate fingers formed on the backup member. The retaining member may define a weakened portion between the body portion and the frangible portion. The weakened portion may define perforations.

In some embodiments, the head assembly may further include a cam latch member positioned to prevent movement of the backup member from the second position to the first position. The head assembly may be pivotally secured to the center rod about a pivot member and the cam latch member may be pivotally mounted about the pivot member. The cam latch member may be configured to maintain engagement with the backup member when the head assembly moves from the non-tilted position to the tilted position such that movement of the backup member from its second position towards its first position is prevented. The cam latch member may be positioned to engage an inner periphery of the backup member when the backup member is in its first position. The anvil assembly may further include a plunger which is urged by a biasing member into engagement with the cam latch member to urge the cam latch member to its pivoted position. The cam latch member may include a curved surface which is configured to eliminate any gap between the cam latch member and the backup member during movement of the head assembly from the first position to the second position.

In various embodiments, the backup member may include a cutting ring and a backup plate. The cutting ring may be secured to a proximal face of the backup plate. The backup plate may include at least one finger positioned to engage a surface of the center rod when the backup member is in its first position to prevent pivotal movement of the head assembly in relation to the center rod. The cutting ring may be formed from a softer material than the backup plate. The cutting ring may be formed from polyethylene and the backup plate is formed from a metal. The center rod may define a longitudinal axis and a pivot axis of the head assembly intersects the longitudinal axis of the center rod.

BRIEF DESCRIPTION OF THE DRAWINGS

Various embodiments of the presently disclosed anvil assembly are disclosed herein with reference to the drawings wherein:

FIG. 3 is a side perspective view with parts separated of the anvil assembly shown in FIGS. 2 and 3;

FIG. 4 is a side perspective view of the cam latch member of the anvil assembly shown in FIGS. 1-3;

DETAILED DESCRIPTION OF EMBODIMENTS

Figure 1:
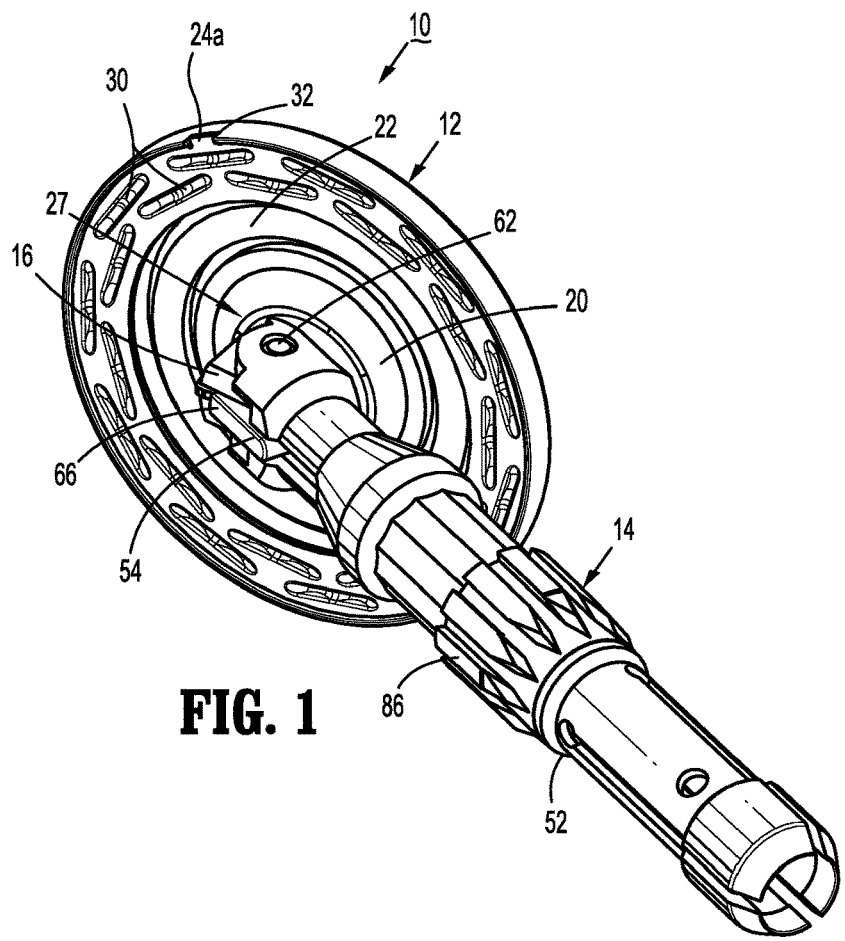
FIG. 1 is a side perspective view from one end of the presently disclosed anvil assembly with the anvil head tilted.

Embodiments of the presently disclosed anvil assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 2:
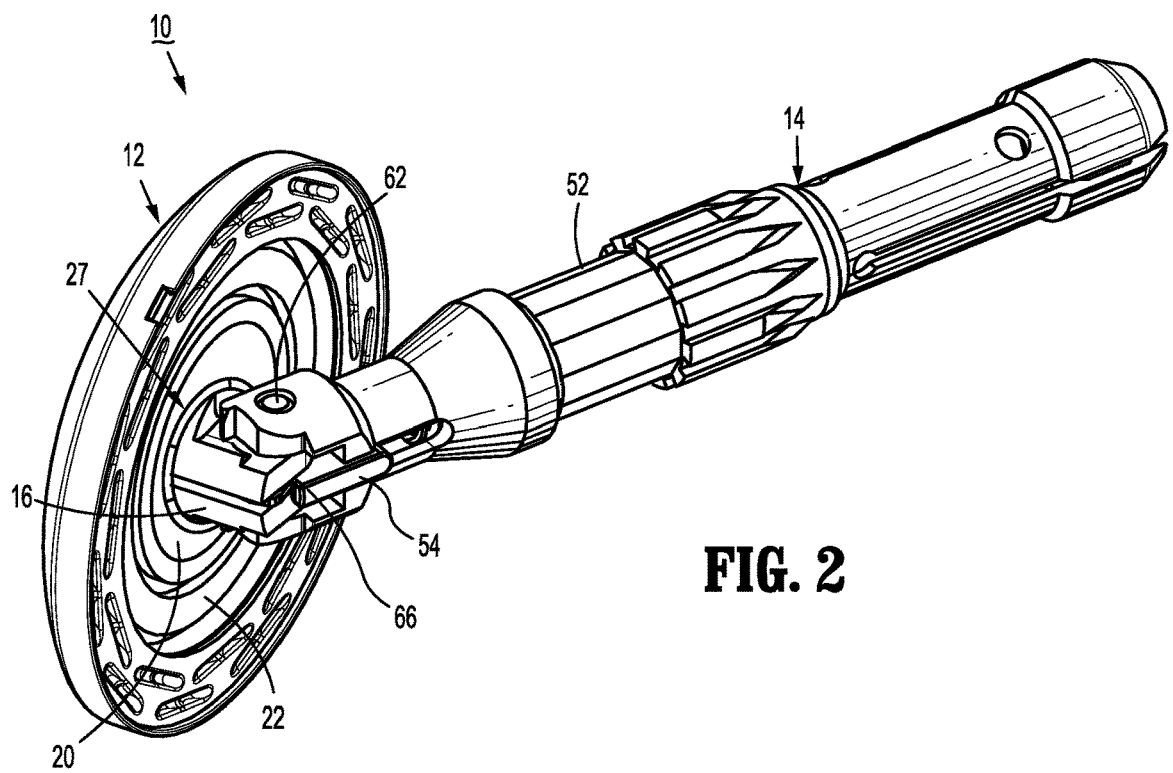
FIG. 2 is a side perspective view from the other end of the anvil assembly shown in FIG. 1.

FIGS. 1-9 illustrate an anvil assembly 10 which is suitable for use with a surgical stapling device for performing, for example, circular anastomoses of hollow tissue organs and hemorrhoid surgeries. Referring to FIGS. 1-3, anvil assembly 10 includes a head assembly 12 and a center rod assembly 14. Head assembly 12 includes a post 16, a housing 18, a backup member or plate 20, a cutting ring 22, a cutting ring cover 23, an anvil plate 24, a cam latch member 26, and a frangible retaining member 27. As shown, post 16 is monolithically formed with and centrally positioned within head 18. Alternately, head 18 and post 16 may be formed separately and fastened together using a known fastening technique, e.g., adhesive, welding, friction fit, etc. Anvil plate 24 is supported in an outer annular recess 28 (FIG. 3) of housing 18 and includes a plurality of staple deforming pockets 30 for receiving and deforming staples. At least one tab 24a extends radially outwardly from anvil plate 24 and is received within a cutout 32 formed in an outer rim of housing 18. Tab 24a and cutout 32 function to align or properly position anvil plate 24 within annular recess 28 of housing 18.

With particular reference now to FIG. 3, backup plate 20 includes a central opening 34 which allows backup plate 20 to be positioned about post 16. Backup plate 20 is configured to be received within an inner annular recess 36 of housing 18 formed between post 16 and outer annular recess 28. Backup plate 20 includes a raised platform 20a. Although platform 20a is illustrated as having a circular shape, other configurations are envisioned, e.g., square, rectangular, triangular, etc. Backup plate 20 includes a pair of inwardly extending fingers 38 which will be described in further detail below. Backup plate 20 is formed from a relatively hard material, e.g., a metal. Alternately other materials of construction may be used to construct backup plate 20.

Figure 6:
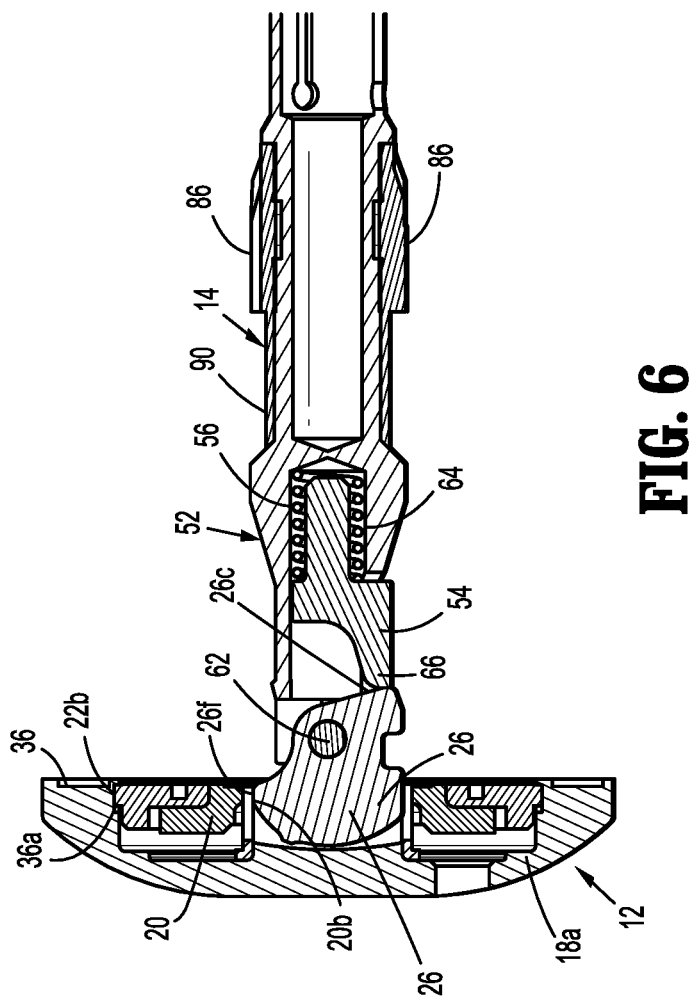
FIG. 6 is a side cross-sectional view of the anvil head and distal end of the center rod assembly taken through the cam latch member with the anvil head in the non-tilted or operative position.

Cutting ring 22 includes an opening 22a having a configuration substantially the same as platform 20a of backup plate 20. Cutting ring 22 includes an outer lip 22b configured to be received within an annular groove 36a formed in housing 18 (FIG. 6). As will be described in further detail below, outer lip 22b of cutting ring 22 is configured to maintain cutting ring 22 and backup plate 20 in a proximal position about post 16 and within inner annular recess 36 of housing 18 prior to a staple forming procedure. Cutting ring 22 may be formed from polyethylene or other suitable material. Cutting ring 22 is fixedly secured to backup plate 20 using, for example, an adhesive, to form a backup plate/cutting ring assembly. In one embodiment, cutting ring 22 is over-molded to backup plate 20 with undercuts. Alternatively, backup plate 20 and cutting ring 22 may be formed as a single or unitary structure.

With reference still to FIG. 3, cutting ring cover 23 is configured to be secured to an outwardly facing or proximal surface 40 of cutting ring 22 using, for example, an adhesive. In one embodiment, cutting ring cover 23 is formed from a material or materials which have a hardness greater than that of cutting ring 22, e.g., Mylar. In other embodiments, cutting ring cover 23 includes two layers of Mylar (not shown) which are joined together using an adhesive and/or a polypropylene coating. Alternately, cutting ring 22 need not have a cover.

Backup plate 20 and cutting ring 22 are configured to be movably mounted about post 16. As will be described in further detail below, backup plate 20 and cutting ring 22 are configured to move from an initial or proximal position (FIGS. 6 and 7) about post 16 and within inner annular recess 36 of housing 18 to an advanced or distal position (FIG. 8) about post 16 and within inner annular recess 36 of housing 18. As discussed in further detail below, in the proximal position, backup plate 20 prevents head assembly 12 from rotating relative to center rod assembly 14 and, in the distal position, backup plate 20 does not prevent head assembly 12 from rotating relative to center rod assembly 14.

With reference still to FIG. 1-3, center rod assembly 14 includes a center rod 52, a plunger 54, and plunger spring 56. A first end of center rod 52 includes a pair of arms 59 which define a cavity 59a (FIG. 3). Each arm 59 has a transverse throughbore 58 which is aligned with a central longitudinal axis of center rod 52. Alternately, throughbores 58 can be offset from the longitudinal axis of center rod 52. Post 16 of anvil head assembly 12 is dimensioned to be positioned within cavity 59a and also includes a transverse throughbore 60. A pivot member 62 pivotably secures post 16 to center rod 52 via throughbore 58 of each arm 59 and throughbore 60 of post 16 such that anvil head assembly 12 is pivotally mounted to center rod assembly 14. For a more detailed description of center rod assembly 14, please refer to the '581 publication, the content of which was previously incorporated herein by reference.

With reference now to FIGS. 3 and 4, cam latch member 26 includes a body 26a having a throughbore 26b. Throughbore 26b is dimensioned to receive pivot member 62 such that cam latch member 26 is pivotally mounted within a transverse slot 72 (FIG. 3) of post 16 about pivot member 62. Cam latch member 26 includes a first body portion 26c which is configured to extend partially from slot 72 of post 16 and be positioned for engagement by finger 66 of plunger 54. Cam latch member 26 also includes an edge 26f which is configured to be urged into engagement with an inner periphery of backup plate 20 by finger 66 of plunger 54 when anvil head 12 is in its non-tilted or operative position (FIG. 6).

Figure 5:
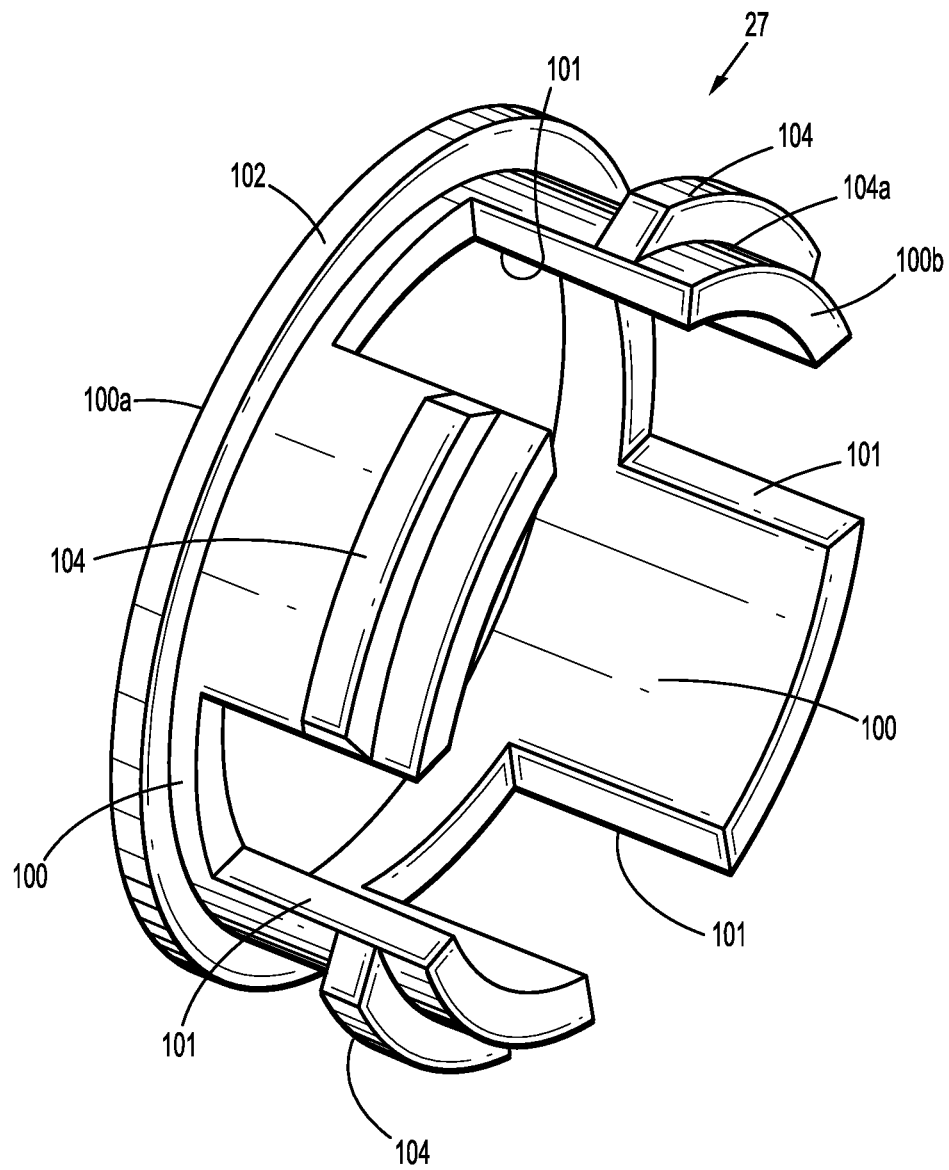
FIG. 5 is a side perspective view of the frangible retainer member of the anvil assembly shown in FIGS. 1-3.
Figure 7:
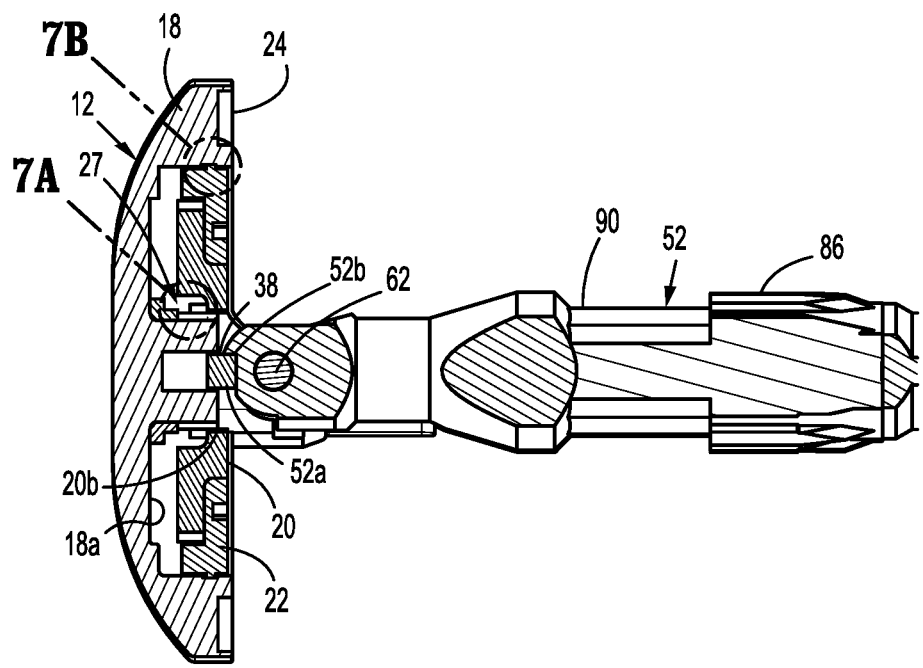
FIG. 7 is a side cross-sectional view of the anvil head and distal end of the center rod assembly with backup plate and cutting ring in their proximal position in the anvil head housing.

With reference now to FIG. 5, frangible retainer member 27 has a first end 100a and a second end 100b and includes a substantially annular body portion 100 having a retaining ring or portion 102 formed near first end 100a and a frangible ring or portion 104 spaced from retaining portion 102 and formed adjacent second end 100b. Retaining ring 102 is configured to secure frangible retainer member 27 about post 16 of head assembly 12. As will be discussed in further detail below, frangible ring 104 is configured to selectively maintain backup plate 20 and cutting ring 22 in the proximal position (FIGS. 6 and 7). Frangible ring 104 may include a stress riser or groove 104a, perforations, or another weakened portion or portions disposed between frangible ring 104 and annular body portion 100 to aid in separation of frangible ring 104 from annular member 100. Frangible retainer member 27 defines a plurality of cutouts 101 configured to accommodate fingers 38 (FIG. 7) of backup plate 20 and cam latch member 26 (FIG. 6).

When frangible retainer member 27 is positioned about post 16, retaining ring 102 is positioned adjacent a back wall 18a of housing 18. Frangible ring 104 is positioned between backup plate 20 and housing 18. Frangible ring 104 is configured to maintain backup plate 20 and cutting ring 22 in the proximal position (FIGS. 6 and 7) until a predetermined force sufficient to fracture or separate frangible ring 104 from annular body portion 100 is applied to the backup plate/cutting ring assembly. The predetermined force can be close to but is less than the force applied by an annular cutting blade (not shown) of a surgical stapling device (not shown) to backup plate 20 (FIG. 3) when the knife blade engages the backup plate/cutting ring assembly. In one embodiment, the predetermined force is between about ten pounds and about ninety pounds. In another embodiment, the predetermined force is about thirty (30) pounds. When the predetermined force is reached, e.g., during cutting of tissue, frangible ring 104 fractures or separates from annular body 100, thereby allowing backup plate 20 to be pushed distally within inner annular recess 36 of housing 18. In any of the embodiments disclosed herein, frangible retainer member 27 may have a continuous ring without cutouts 101 so that the parts stay together. The four sections formed by cutouts 101 could become jammed, preventing the anvil from tilting.

Figure 7A:
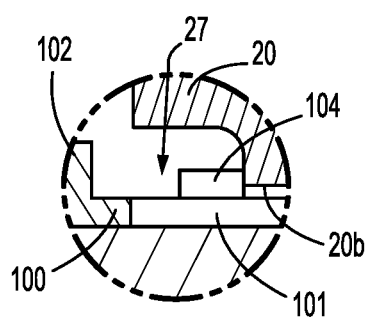
FIG. 7A is an enlarged view of indicated area 7A shown in FIG. 7.
Figure 7B:
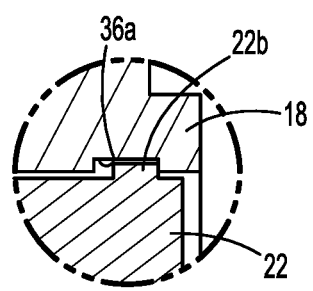
FIG. 7B is an enlarged view of indicated area 7B shown in FIG. 7.

Referring to FIGS. 6 and 7, anvil assembly 10 is shown in a pre-fired, operative position. In the pre-fired, operative position, backup plate 20 is spaced from back wall 18a of housing 18 and fingers 38 (FIG. 7) of backup plate 20 engage protrusions 52b formed adjacent top surface 52a of center rod 52 to prevent tilting of anvil head assembly 12 about pivot member 62. As shown in FIG. 6, finger 66 of plunger 54 is urged by spring 56 into engagement with body portion 26c of cam latch member 26 to urge cam latch member 26 in a clockwise direction about pivot member 62 such that edge 26f of cam latch member 26 engages an inner periphery 20b of backup member 20. Frangible retainer member 27 prevents inadvertent or premature movement of backup plate 20 distally within inner annular recess 36 of housing 18 to prevent premature or inadvertent tilting of anvil head assembly 12. Specifically, and with particular reference to FIG. 7A, backup plate 20 engages frangible ring 104 of frangible retaining member 27, thereby maintaining backup plate 20 in the proximal position. With particular reference to FIG. 7B, backup plate 20 is further maintained in the proximal position within inner annular recess 36 of housing 18 through receipt of lip 22b of cutting ring 22 within annular groove 36a of housing 18.

Figure 8:
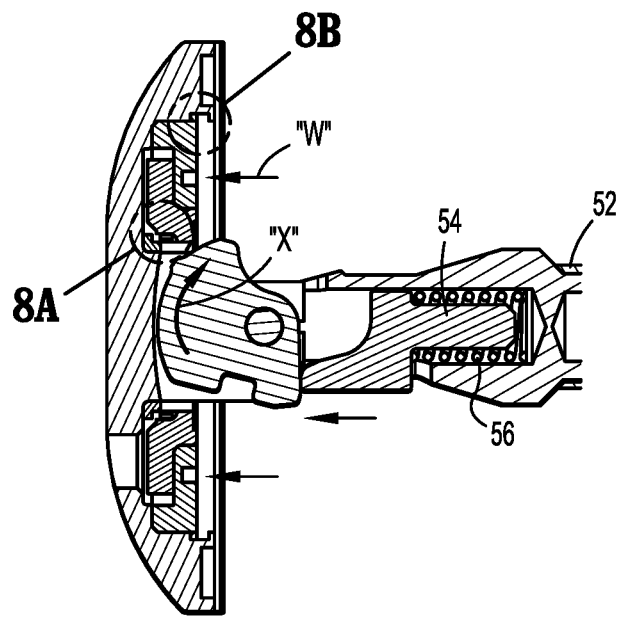
FIG. 8 is a side cross-sectional view of the anvil head and distal end of the center rod assembly taken through the cam latch member prior to tilting of the anvil head with the backup plate and cutting ring in their advanced or distal position in the anvil head housing.
Figure 8A:
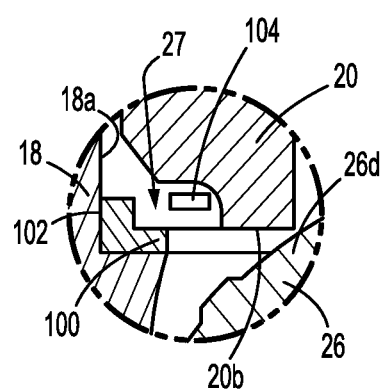
FIG. 8A is an enlarged view of indicated area 8A shown in FIG. 8.

During a stapling procedure, anvil assembly 10 is attached to a surgical stapling device (not shown) and the surgical stapling device is fired in the manner described in the '060 patent, the content of which was previously incorporated herein by reference. With reference now to FIG. 8, during firing of the surgical stapling device, a knife blade (not shown) of the surgical stapling device engages cutting ring 22 (or cutting ring cover 23) and applies a distal force on the backup plate/cutting ring assembly 20/22. As described above, when a predetermined force is applied to the backup plate/cutting ring assembly, the force is transferred through the backup plate/cutting ring assembly 20/22 to frangible ring 104 of frangible retaining member 27. Upon application of the predetermined force to frangible ring 104, frangible ring 104 separates from annular body portion 100 of frangible retaining member 27 to allow the backup plate/cutting ring assembly 20/22 to be pushed distally, in the direction indicated by arrow "W", into inner annular recess 36 of housing 18. The distal movement of the backup plate/cutting ring assembly 20/22 causes fingers 38 (FIG. 7) of backup plate 20 to move away from and out of engagement with protrusions 52b (FIG. 7) of center rod 52. As inner periphery 20b of backup plate 20 moves past edge 26f of cam latch member 26, cam latch member 26 is pivoted, in the direction indicated by arrow "X" in FIG. 8, by plunger 54 to a position in which body portion 26d is positioned in front of and engages backup plate 20 (FIG. 8A). Engagement of plunger 54 with cam latch member 26 and subsequently with post 16 urges anvil head assembly 12 towards the tilted position.

With particular reference to FIG. 8A, during distal movement of backup plate/cutting ring assembly 20/22, frangible ring 104 of frangible retaining member 27 is separated from annular body portion 100 of frangible retaining member 27 and moved distally. Separate frangible ring 104 remains trapped between back wall 18a of housing 18 and backup plate/cutting ring assembly 20/22.

Figure 8B:
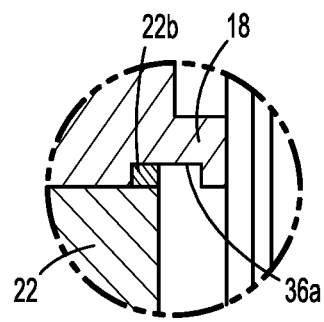
FIG. 8B is an enlarged view of indicated area 8B shown in FIG. 8.

With particular reference now to FIG. 8B, in addition to separation of frangible ring 104 from annular body 100, distal movement of backup plate/cutting ring assembly 20/22 causes lip 22b formed on cutting ring 22 to be sheared off from the body portion of cutting ring 22. Lip 22b remains within groove 36a of housing 18. Alternatively, the knife blade (not shown) of the surgical stapling device (not shown) may cut through cutting ring 22, thereby separating the portion of cutting ring 22 that includes lip 22b from the remainder of cutting ring 22. The portion of cutting ring 22 that includes lip 22b remains within groove 36a of housing 18.

It is noted that anvil head assembly 12 will not immediately tilt upon firing of a surgical stapling device (not shown) because, upon firing, anvil head assembly 12 is in an approximated position, i.e., the anvil head assembly 12 is in close alignment with the shell assembly of the stapling device (not shown). As such, the tilting of anvil head assembly 12 is prevented by engagement with the shell assembly (not shown) of the surgical stapling device (not shown) until anvil head assembly 12 is unapproximated.

Figure 9:
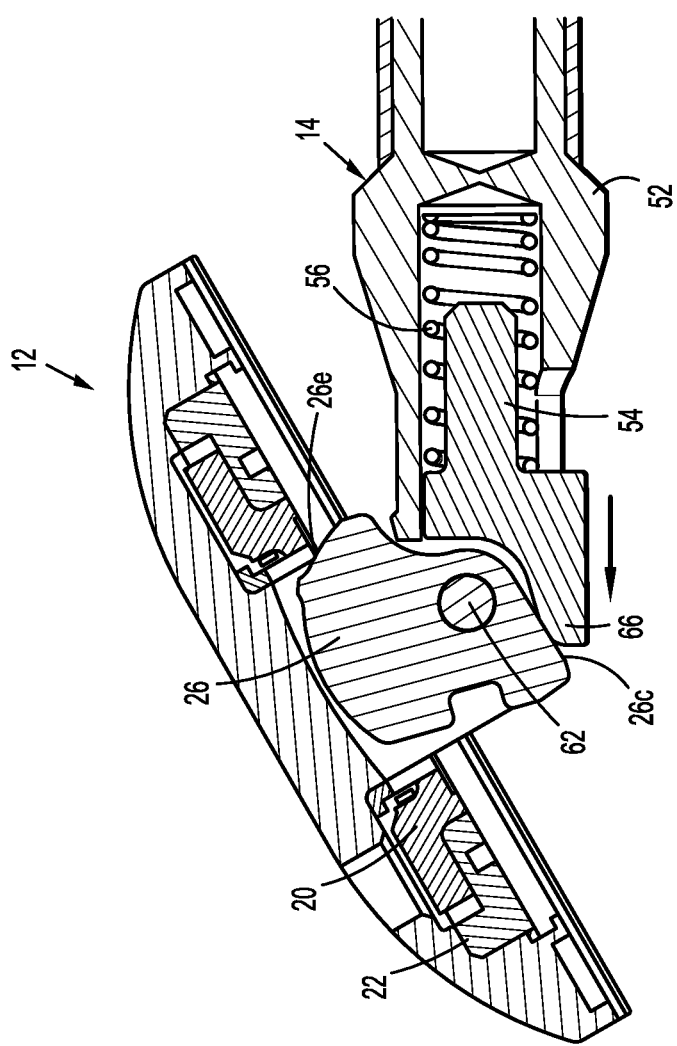
FIG. 9 is a side cross-sectional view of the anvil head and distal end of the anvil center rod assembly with the backup plate and cutting ring in their advanced position in the anvil head housing and the anvil head in the tilted position.

Referring to FIG. 9, as anvil head assembly 12 pivots towards its tilted position, finger 66 of plunger 54 maintains surface 26e of cam latch member 26 in contact with backup plate 20 to prevent backup plate 20 from sticking to the knife blade (not shown) of the surgical stapling device as the knife blade is retracted. It is noted that curved surface 26e of cam latch member 26 is configured to eliminate any gap and ensure contact between surface 26e of cam latch member 26 and backup plate 20 to hold backup plate 20 in place during and after the knife blade is retracted such that backup plate/cutting ring assembly 20/22 stays in the distal position during tilting of anvil assembly 12.

It will be understood that various modifications may be made to the embodiments disclosed herein. For example, although shown having an annular configuration, the frangible retaining member may have other configurations, e.g., square, oval, rectangular, etc. Therefore, the above description should not be construed as limiting, but merely as exemplifications of preferred embodiments. Those skilled in the art will envision other modifications within the scope and spirit of the claims appended hereto.

What is claimed is:

1. An anvil assembly comprising:
   a center rod assembly configured for releasable connection to a surgical stapler; and
   a head assembly including a housing, a backup member, and a retaining member, the head assembly being supported on the center rod assembly from a non-tilted position to a tilted position, wherein the backup member is supported by the housing and movable from a first position in which a portion of the backup member is positioned to prevent pivotal movement of the head assembly relative to the center rod assembly, to a second position in which the backup member is positioned to permit pivotal movement of the head assembly relative to the center rod assembly, the retaining member including a body portion disposed radially inward of the backup member and fixed relative to the housing during movement of the backup member, and a frangible portion separable from the body portion, the frangible portion being engaged with the backup member, wherein separation of the frangible portion from the body portion permits movement of the backup member from the first position to the second position.

2. The anvil assembly according to claim 1, wherein the retaining member is positioned in the head assembly to prevent movement of the backup member from the first position to the second position until the frangible portion of the retainer member separates from the body portion.

3. The anvil assembly according to claim 1, wherein the frangible portion of the retaining member is configured to separate from the body portion of the retaining member when a predetermined force is applied to the backup member.

4. The anvil assembly according to claim 1, wherein the frangible portion of the retaining member is positioned in the head assembly between the housing and the backup member, the retaining member further including a retaining portion formed on a first end of the body portion.

5. The anvil assembly according to claim 4, wherein the retaining portion of the retaining member is positioned adjacent an inside wall of the housing.

6. The anvil assembly of claim 4, wherein the frangible portion is supported on the body portion at a location spaced from the retaining portion.

7. The anvil assembly according to claim 1, wherein the head assembly further includes a post, the housing and the post defining an annular recess and the retaining member being positioned in the annular recess.

8. The anvil assembly of claim 1, wherein the body portion of the retaining member defines at least one cutout and the backup member includes at least one finger, the at least one cutout being configured to accommodate the at least one finger.

9. The anvil assembly of claim 1, wherein the retaining member defines a weakened portion between the body portion and the frangible portion.

10. The anvil assembly of claim 9, wherein the weakened portion defines perforations.

11. The anvil assembly of claim 1, wherein the head assembly further includes a cam latch member, the cam latch member positioned to prevent movement of the backup member from the second position to the first position.

12. The anvil assembly according to claim 11, wherein the head assembly is pivotally secured to the center rod about a pivot member, the cam latch member being pivotally mounted about the pivot member.

13. The anvil assembly according to claim 1, wherein the head assembly further includes a cam latch member, the cam latch member being configured to maintain engagement with the backup member when the head assembly moves from the non-tilted position to the tilted position such that movement of the backup member from the second position towards the first position is prevented.

14. The anvil assembly according to claim 13, wherein the cam latch member is positioned to engage an inner periphery of the backup member when the backup member is in the first position.

15. The anvil assembly according to claim 13, further including a plunger and a biasing member, the plunger being urged by a biasing member into engagement with the cam latch member to urge the cam latch member to the pivoted position.

16. The anvil assembly according to claim 13, wherein the cam latch member includes a curved surface which is configured to eliminate any gap between the cam latch member and the backup member during pivotal movement of the head assembly from the first position to the second position.

17. The anvil assembly according to claim 1, wherein the backup member includes a cutting ring and a backup plate, the cutting ring being secured to a proximal face of the backup plate.

18. The anvil assembly according to claim 17, wherein the backup plate includes at least one finger positioned to engage the center rod when the backup member is in the first position to prevent pivotal movement of the head assembly in relation to the center rod.

19. The anvil assembly according to claim 18, wherein the cutting ring is formed from polyethylene and the backup plate is formed from a metal.

20. The anvil assembly according to claim 17, wherein the cutting ring is formed from a softer material than the backup plate.

* * * * *